United States Patent [19]

Ritchart et al.

[11] Patent Number: 5,209,737
[45] Date of Patent: May 11, 1993

[54] LEVER ACTUATED SEPTUM SEAL

[75] Inventors: Mark A. Ritchart, Murrieta; Robert P. Cooper, Yorba Linda; Charles C. Hart; Donald L. Gadberry, both of Huntington Beach, all of Calif.

[73] Assignee: Applied Medical Resources, Inc., Laguna Hills, Calif.

[21] Appl. No.: 732,141

[22] Filed: Jul. 18, 1991

[51] Int. Cl.5 .................................. A61M 5/178
[52] U.S. Cl. .............................. 604/167; 604/256
[58] Field of Search .......... 604/167, 169, 160, 161, 604/256, 164, 236, 200, 201, 202, 205, 264, 165, 166, 905; 251/149.1; 137/843, 844, 845, 849

[56] References Cited

U.S. PATENT DOCUMENTS 4,723,550 2/1988 Bales et al. ..................... 604/256
4,842,591 6/1989 Luther ........................... 604/167

Primary Examiner—Cary E. O'Connor
Attorney, Agent, or Firm—Richard L. Myers

[57] ABSTRACT

A septum valve in a trocar assembly has a variable orifice that is responsive to a cross-sectional dimension of the surgical instrument being inserted into the trocar channel, thereby minimizing leakage of inflation gas from the body cavity, such as the abdomen, being operated on. An elastomeric septum is disposed in the channel and includes portions which define an orifice having in a relaxed state a first cross-sectional area. An actuation assembly provided with levers which pivot radially outwardly to expand the seal and thereby expand the orifice to the second cross-sectional area in response to entry of the instrument into the channel. The actuation assembly is free to float in an annular recess to accommodate an instrument which is misaligned with the trocar channel.

32 Claims, 4 Drawing Sheets

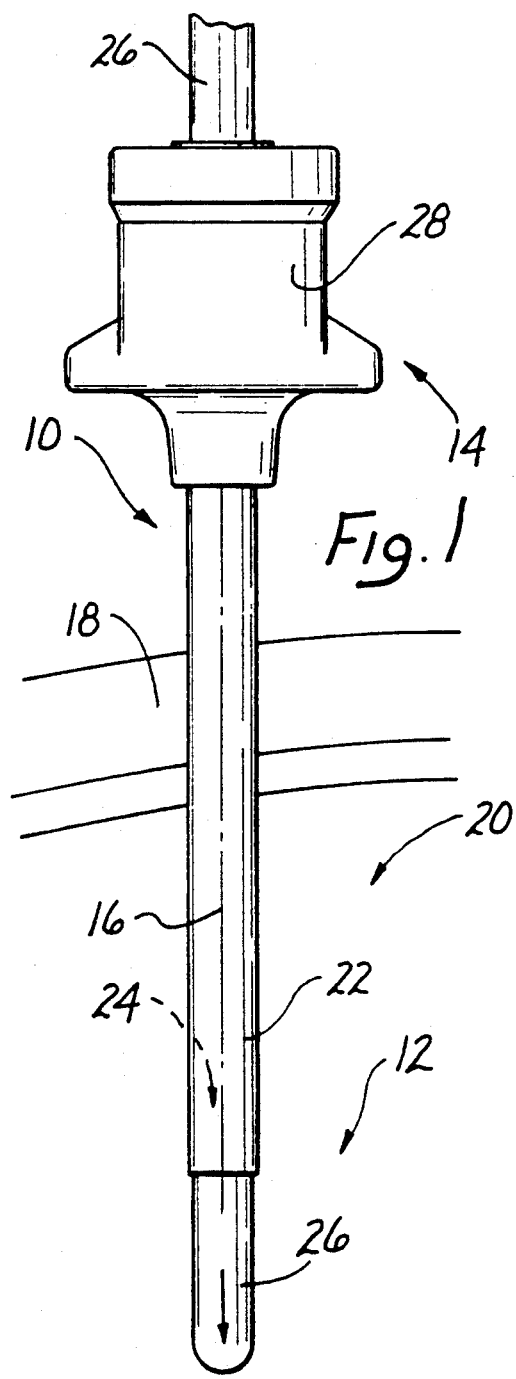
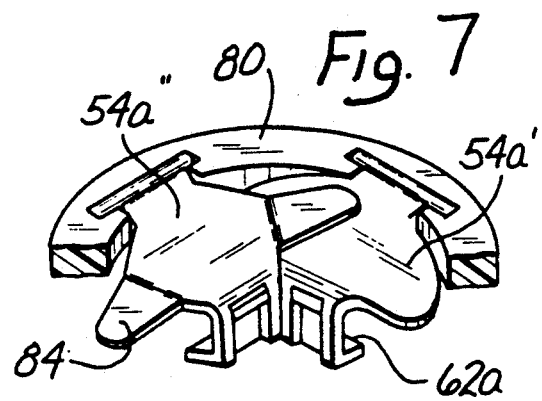
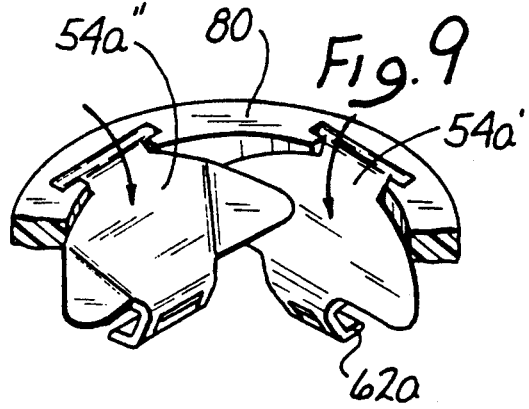
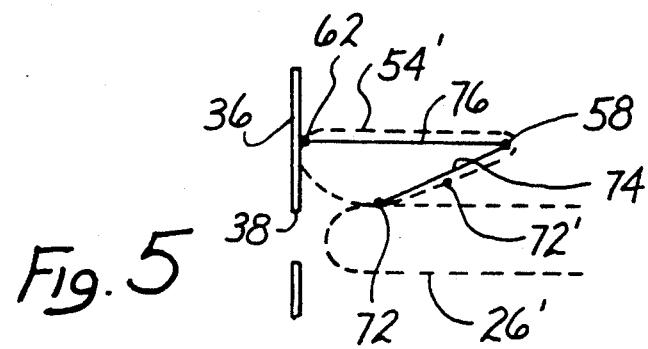

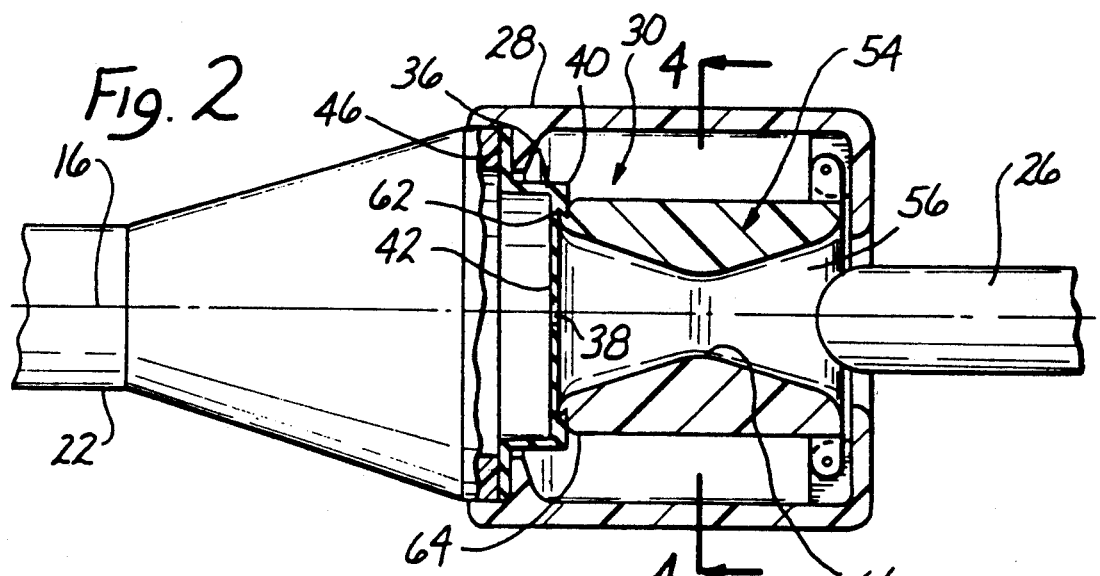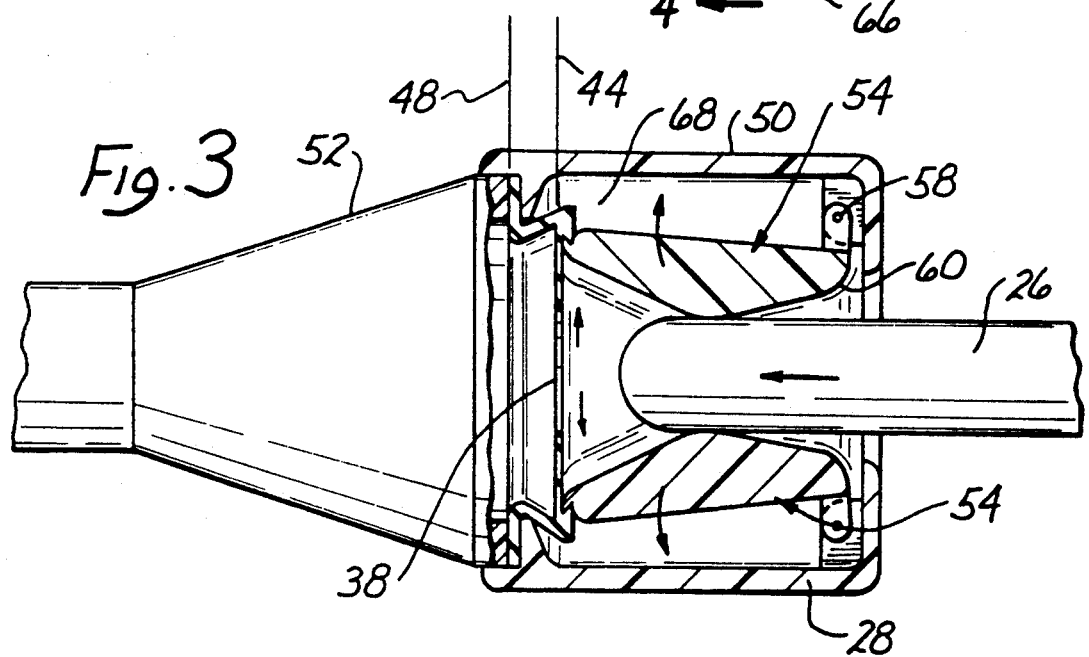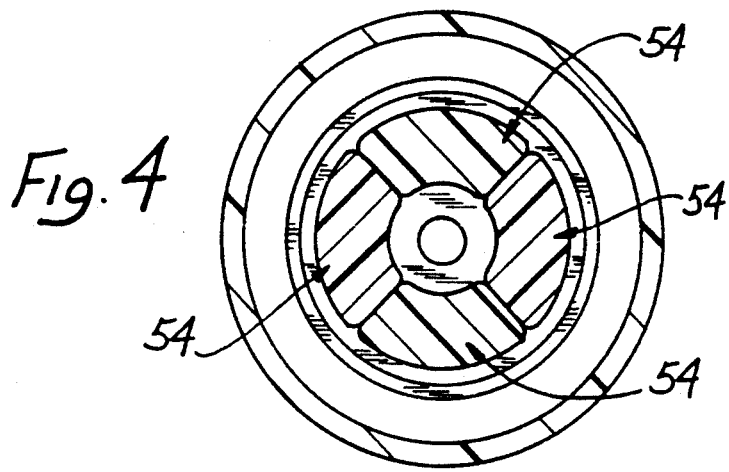

LEVER ACTUATED SEPTUM SEAL

BACKGROUND OF THE INVENTION

1. Field of the Invention

This invention relates generally to elastomeric septums which are adapted to form seals around tubes and shafts and more specifically to septums in surgical trocars which form seals around elongate surgical instruments.

2. Discussion of the Prior Art

In recent times, noninvasive surgery has advanced to the point though tubular devices and the surgical procedures performed with long narrow instruments through those access devices. These access devices are referred to as trocars. Trocars typically include a puncturing device, commonly referred to as an obturator, and a closely spaced outer sheath or cannula. To insert the cannula for use, the integral obturator and associated sleeve assembly pierces through the abdominal wall until it just enters the abdominal cavity. The obturator is then removed, leaving the cannula in place and allowing access to the abdominal cavity from outside the body of the patient. In performing the abdominal surgery, rather than laying the patient open, several of these trocars can be inserted through respective incisions that are approximately a centimeter in diameter. When inserted through the abdominal wall, the trocar provides a channel through which surgical instruments can be inserted to accomplish various objectives such as visualization, cutting, irrigating, aspirating, grinding, traction, and removal of body parts such as a gall bladder.

In order to provide space within which to operate, the abdominal cavity is usually inflated with an insufflation gas. Maintenance of this inflation pressure is of particular concern to the trocar art. Thus, trocars are typically provided with septum valves of various sizes and configurations which can form seals around the surgical instruments being inserted through the trocar. However since these instruments have different cross-sectional shapes and sizes, the seals tend to leak, form "cat-eyes", or generate significant friction forces which inhibit axial movement of the surgical instruments.

The need has remained for a septum seal which has a variable aperture through which instruments of different cross-sectional sizes may pass. The aperture should conform tightly to the cross-sectional configuration of the instrument without unduly restricting the passage of the instrument therethrough, thus minimizing leakage of the seal while maintaining reasonably free instrument access to the abdominal cavity.

SUMMARY OF THE INVENTION

The invention solves the problem outlined above by employing a septum valve in a trocar assembly which has a variable orifice that is responsive to the cross-sectional area of the instrument being inserted into the trocar channel. This is an advantageous approach because the seal is, in essence, customized to the specific cross-sectional area of the particular instrument actually being used at any given time. This tends to avoid the leakage problem caused by a poor fit between the seal and the instrument, and also minimized the problem of frictional resistance to entry of the instrument caused by a seal which affords too small an aperture to accommodate the instrument being inserted. Another advantage is that the seal may completely seal the aperture when the trocar is not being used, if desired.

In one aspect of the invention, a trocar assembly is provided which includes a channel defined along an elongate axis and which is adapted to receive an instrument having a particular cross-sectional area. An elastomeric septum is disposed in the channel and includes portions which define an orifice having, in a relaxed state, a first cross-sectional area and in an expanded state a second cross-sectional area. The trocar assembly includes means which are responsive to the entering instrument for expanding the orifice to the second cross-sectional area. Two orifice embodiments are contemplated. In one embodiment, the first cross-sectional area of the orifice is substantially zero. This would ensure that leakage of insufflation gas from the abdominal cavity is substantially eliminated when no instrument is present in the channel. In a second embodiment, the first cross-sectional area of the orifice is greater than zero. This second embodiment may be preferred under certain circumstances, such as when it is desired to view the interior of the abdomen by means of a fiber optic tube. Such a tube may be too small in cross-section and too resilient to actuate the orifice expansion means, but would be capable of fitting through the first, very small cross-sectional area of the orifice without causing unacceptable leakage of the gas.

In another aspect of the invention, the trocar assembly includes a lever having a distal end and a proximal end. The proximal end of the lever is pivotal on an axis which lies transverse to the elongate axis of the trocar assembly. Means is carried by the lever at its distal end for engaging and stretching the septum, thereby expanding the orifice. Between the proximal end and the distal end of the lever is disposed a means for sensing the particular cross-sectional area of the instrument upon its entry into the channel, and moving the lever distal end a radial distance sufficient to expand the orifice to the second cross-sectional area. The lever is configured like an elbow, being contoured radially inwardly from each end to a convergence point between distal and proximal ends. This convergence point is the instrument sensing means because the channel is at its narrowest at this point and is narrower than the cross-sectional area of the instrument. Therefore, the instrument pushes the levers radially outwardly as it approaches this convergence point.

In yet another aspect of the invention, a valve assembly is provided which is adapted to receive an instrument having an outer surface and a cross-sectional dimension. The valve assembly includes a housing which defines a channel that extends along an elongate axis. A septum is disposed in the housing and extends across the channel. Portions of the septum are formed of an elastomeric material and are expandable radially outwardly to enlarge the orifice. Means for enlarging the orifice are pivotal on the housing and engage the septum outwardly of the orifice to enlarge it. These enlarging means are responsive to the instrument to enlarge the orifice in proportion to the cross-sectional dimension of the instrument. In this manner, the orifice is expanded precisely the correct amount to accommodate the instrument's passage without excessive leakage or resistance.

The above mentioned and other features and advantages of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 is a side elevation of a trocar assembly of the type used in this invention, operatively positioned to penetrate a tissue barrier;

FIG. 2 is an axial cross-sectional view of the trocar, showing details of an embodiment of a valve assembly prior to insertion of a surgical instrument therein;

FIG. 3 is an axial cross-section view similar to that of FIG. 2, showing details of the same embodiment of the trocar valve assembly during insertion of the surgical instrument;

FIG. 4 is a cross-sectional view along lines 4—4 for FIG. 2, showing additional details of the valve assembly;

FIG. 5 is a top plan view of a modified embodiment of the trocar valve assembly, showing a different hinge arrangement for a plurality of septum levers;

FIG. 7 is a perspective view of one half of the septum levers and associated peripheral ring illustrated in FIG. 6;

FIG. 9 is a perspective view of one half of the septum levers and associated peripheral ring illustrated in FIG. 8;

DESCRIPTION OF PREFERRED EMBODIMENTS

Figure 10:
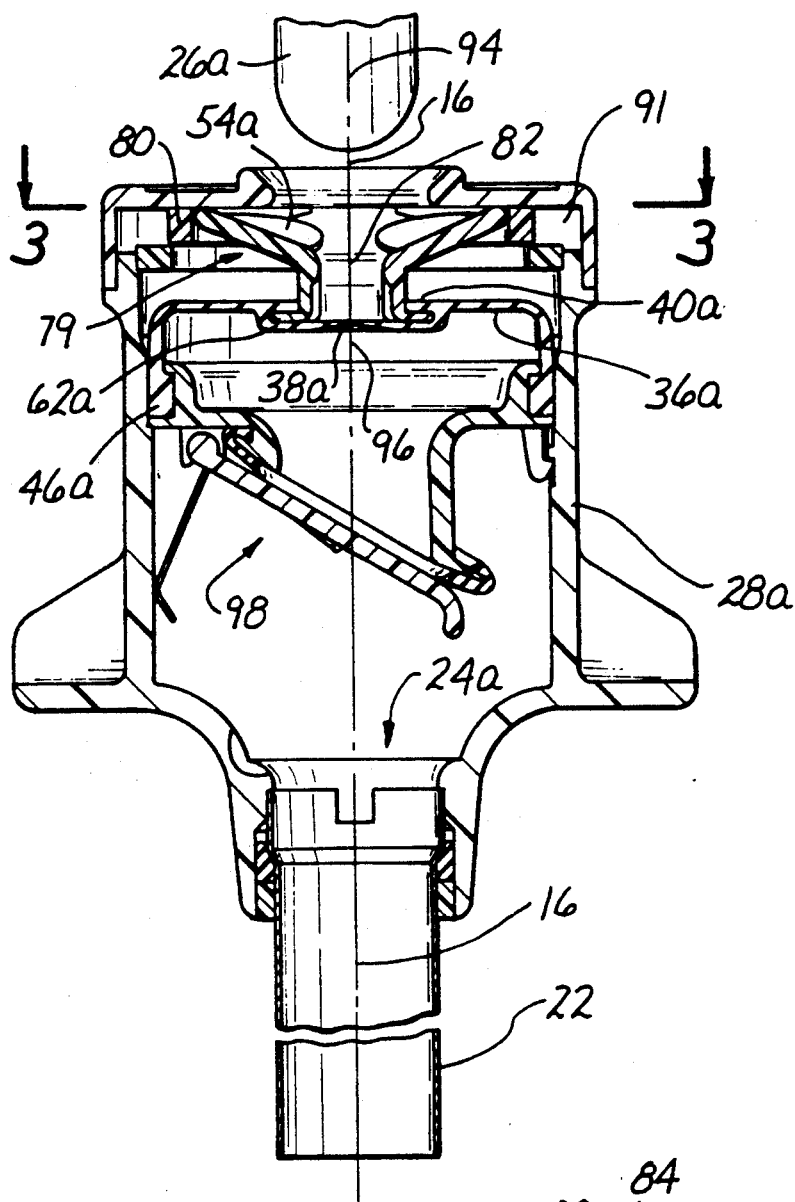
FIG. 10 is an axial cross-section view of a further embodiment of the trocar with the septum levers operatively disposed relative to a trap valve assembly prior to insertion of a surgical instrument.

A surgical trocar is illustrated in FIG. 1 and designated generally by the reference numeral 10. The trocar 10 is a narrow elongate instrument having a distal end 12 and a proximal end 14. It is typically configured along a longitudinal axis 16 and is generally circular in radial cross-section.

It is the purpose of the trocar 10 to provide a channel through a tissue barrier in order to provide access across the barrier into a body cavity. By way of example, an abdominal wall 18 is illustrated in FIG. 1, on the other side of which is an abdominal cavity 20. The trocar 10 typically includes an elongate tube or cannula 22 having a cylindrical configuration and a wall thickness which may be on the order of 0.015 to 0.030 inches. The cannula has an interior bore or channel 24 which may have a diameter measuring in a range between 5 and 12 millimeters. The trocar 10 is designed to pierce, cut, incise, or otherwise puncture the tissue barrier, such as the abdominal wall 18, and to leave the cannula 22 extending through the incision. Elongate surgical devices of varying diameter such as cutters, clamps, traction devices, visualization devices, aspirators and irrigators, and other instruments 26 can be positioned and manipulated to perform a particular surgical procedure within the cavity 20.

The trocar 10 includes a valve housing 28 which encloses a valve mechanism 30 such as that shown in FIGS. 2-4. These Figures illustrate the trocar 10 at a point in time after it has been inserted through the abdominal wall 18 leaving the cannula 22 to provide access to the abdominal 20.

The valving mechanism 30 includes a septum 36, which is preferably molded from an elastomeric material such as C-flex ®, a low durometer polymer manufactured by Concept Polymer Technologies. This material is very soft and can be easily stretched. Of course, other known elastomeric materials could be used instead to accomplish the objectives of the invention.

The seal 36 further includes a central orifice 38 which is centered about the trocar elongate axis 16. The orifice in a relaxed state has a first cross-sectional area which, in a first embodiment may be substantially zero, and in a second embodiment, may be small, but greater than zero. A lip 40 is integrally molded with the seal 36 and lies outwardly of an inner seal portion 42 which defines the orifice 38. In a particular embodiment, the lip 40 comprises a circular ridge which may lie in substantially the same transverse plane 44 as the inner orifice portion 42 of the seal.

Seating portions 46 are integrally molded with the seal 36 and lie radially outwardly of the inner seal portion 42. An important feature of the invention is that the seating portions 46 lie along a transverse plane 48 which is axially offset from plane 44, for reasons to be discussed further below. In this particular embodiment the seating portions 46 are clamped between a septum seal housing 50 and a transition channel housing 52, thereby resiliently supporting and seating the seal 36 within the seal housing 50.

A plurality of levers 54 are disposed outwardly of the elongate axis 16, in such a manner as to define a sealing housing channel 56 therebetween. In a preferred embodiment, four such levers 54 are provided, as shown in FIG. 4, but any number of levers could be employed, with suitable modifications in design.

In this case, the seal housing channel 56 is concentric with trocar channel 22, both lying along common axis 16, with the two channels fluidly communicating through the orifice 38 and the transition channel housing 52. Each lever 54 can be mounted on a pivot 58 and its proximal end 60, with the pivotal axis being transverse to the elongate axis 16. At least one tooth member 62 can be provided at an end 64 of each lever 54. This tooth member 62 is adapted to engage and interlock with the septum seal lip 40. In the illustrated embodiment, the lever teeth collectively form a substantially circular tooth member which engages the circular lip 40 about its circumference. Each lever 54 has a predetermined radial width at its proximal end 60 and a predetermined radial width at its distal end 64. The predetermined width for the proximal end 60 may or may not be substantially the same as that for the distal end. Regardless, from each end 60 or 64 the lever interior surface is contoured radially inwardly, with a configuration like that of an elbow, to a point of maximum width or convergence between the proximal and distal ends 60, 64 respectively. Conversely, the radial width of the channel 56 is at a minimum at this same convergence point, which point becomes essentially the channel throat 66. An open space 68 lies radially outwardly of both the levers 54 and the seal lip 40, within the seal housing 50. This space 68 accommodates expansion of the levers 54 and orifice 38 as described below.

In operation, it may be desired to insert the surgical instrument 26 through the channel 22 and into the body cavity 18. To do so, the instrument 26 is first inserted into the valve housing 28 as shown in FIG. 3. The instrument 26 has a particular cross-sectional area which may vary according to the type of instrument, but it must be greater than the minimum width of the housing 28 at the throat 66 for the levers 54 to be actuated to expand the orifice 38.

As the instrument 26 is pushed into the throat 66 of the channel, its cross-sectional area, which exceeds the width of the channel, pushes the levers 54 radially outwardly, thereby pivoting the levers about their respective pivots 58, and moving the lever distal ends radially outwardly, as shown by the arrows in FIG. 3. Consequently, the engaging relationship between the lever teeth 62 and the lip 40 expands the lip radially outwardly. It is of particular advantage that the seating portions 46 of the seal are axially offset from orifice 38 and the lip 40, as discussed above. This positions the lip so that it is free to expand into the open space 68.

The leverage provided by the levers 54 is best illustrated again by reference to FIG. 3, where it can be seen that the lever arm for measuring the diameter of the instrument 26 is less than the lever arm for spreading the lip 40. The expansion of the lip 40 in turn stretches the inner portions 42 of the septum 36, causing the radial width of the central orifice 38 to be expanded, as shown by the FIG. 3 arrows, to a second cross-sectional area which is slightly smaller than the particular cross-sectional area of the instrument 26. As a result, the instrument 26 may pass through the orifice 38 into the transition channel 52 and the channel 22 fairly easily, with the orifice closing tightly as to create significant frictional resistance between the instrument 26 and the septum 36. Such resistance is to be avoided since it not only opposes forward movement of the instrument 26 but also tends to tear the septum 36.

Operation of the levers 54 can be better understood with reference to the schematic of FIG. 5. In this Figure, the septum 36 is illustrated with the lever and instrument shown by the dotted lines 54' and 26' respectively. The tooth member is shown at a point 62 while the pivot is shown as a point 58. A point of contact between the lever 54' and instrument 26' is designated by the reference numeral 72. A line 74, extending between the points 58 and 72, schematically illustrates a first lever arm. Similarly, a line 76, extending between the points 58 and 62, schematically illustrates a second lever arm.

In operation, the instrument 26' is inserted into the channel 24 toward the orifice 38 in the septum 36. Along this path, the outer surface of the instrument 26' contacts the lever 54' at the point 72. Depending on the radial dimension of the instrument 26' —the diameter in the case of an instrument having a cylindrical shaft or tube—the lever 54' will pivot upwardly about the pivot 58 causing the point 62 to move radially upwardly thereby expanding the diameter of the orifice 38.

The amount of force applied to stretching the septum as a result of this initial insertion of the instrument 26', is dependent upon the configuration of the levers 54'. It can be appreciated that the distance that the point 62 moves as well as the force applied to that movement is dependent upon the length of the respective first and second lever arms 74 and 76. In the illustrated embodiment, the first lever arm 74, which measures the radial dimension of the instrument 26' is shorter than the second lever arm 76 which expands the septum 36. In such a case, the radial stretch of the septum 36 is dependent upon the radial dimension of the instrument 26' in proportion to the ratio of the length of the lever arm 76 to the length of the lever arm 74. The respective lengths of these lever arms 74, 76 can be a matter of design depending on the forces and distances desired for expansion of the septum 36 for given size of the instrument 26'.

It will also be apparent that the surface of the lever 54' which faces the instrument 26' can be configured so that the instrument 26' slides along the surface contacting the lever 54' at a different point 72 as the instrument 26' is inserted. If this point of contact 72 moves along the surface of the lever 54', the length of the first lever arm 74 will vary in length accordingly. In this manner, the desired forces and distances associated with the stretch of the septum can be made to vary in accordance with the proximity of the instrument 26' to the orifice 38. For example, when the instrument 26' is initially inserted, it may contact the lever 54' at a point 72' which would have a shorter lever arm than that associated with the point 72.

A modified embodiment of the valving mechanism 30, showing a different hinge arrangement for the lever 54 is shown in FIGS. 6 through 11. This embodiment is similar to that of FIG. 2 except as described and shown herein. Each of the elements in FIGS. 6-11 corresponding to equivalent elements in FIGS. 2-4 are designated by the same reference numeral, followed by the letter "a".

In this particular embodiment, an actuation mechanism 79 includes a plurality of levers 54a which are radially disposed about a frame 80. This frame is configured in the shape of an annulus having an axis 82 which extends perpendicular to the page in FIG. 6. Again, it is preferred, but no required, that four of the levers 54a be employed. These levers can be arranged as opposing pairs of the levers 54a' and 54a". In the illustrated embodiment, the levers 54a' are disposed distally of the levers 54a".

All of the levers 54a include a pair of wings 84 joined by a central portion 86. In the case of the distal levers 54a', the wings 84 and central portion 86 can be configured to lie in the same place. However, it is advantageous if the proximal levers 54a" are constructed so that the wings 84 pivot on the central portions 86. This pivoting may occur along a line such as that designated 88 in FIG. 6. The pivoting of the wings 84 on the proximal levers 54a" facilitates a funnel configuration for this actuation mechanism 79. As the instrument moves generally along the axis 82 it is probable that it will initially contact the proximal levers 54a". The wings 84 of these proximal levers will press against the distal levers 54a' thereby aiding in the inward compression of the levers 54a' and the radial outward expansion of the septum portions which define the orifice 38.

Each of the levers 54a is mounted on a pivot 58a at its proximal end, and has at least one tooth member 62a at its distal end. This tooth member 62a is adapted to engage the septum lip 40 as previously discussed.

The hinge or pivot 58a can be of the pin and notch variety illustrated or can be constructed as a "living hinge", unitary and integral with the annular frame 80. A "living hinge" may also accommodate the desired bending of the wings 84 with respect to the central portion 86 of the levers 54a".

The septum 36a will vary in thickness depending on the material used in the septum. In an embodiment wherein the septum is formed of the C-flex material previously described, the thickness dimensions also vary radially of the orifice 38a. In general, these dimensions with depend on requirements for strength, sealing, flexibility and rigidity at a particular location.

The portions of the septum which define the orifice 38a need to be sufficiently strong to form the seal with the instrument 26a, but sufficiently flexible to avoid substantial frictions forced which would resist axial movement of the instrument. The thickness of these portions will typically be in a range of 0.040 to 0.080 inches with 0.060 inches preferred.

The lip 40a needs to be relatively firm and to provide some degree of radial compression of elasticity in order to bias the levers 54a toward a closed position. In general, these objectives are accomplished with a thickness between 0.075 and 0.120 inches, with a thickness of 0.100 being most preferred.

Between the lip 40a and the outer perimeter of the septum 36a, a higher degree of flexibility may be desired. In this region, the septum 36a may have a thickness between 0.020 and 0.050 inches, with a thickness of 0.030 inches being chosen for the most preferred embodiment.

At the outer perimeter of the septum 36a, it is desirable to inhance the sealing characteristics between the septum 36a and the housing 28a. In a preferred embodiment the sealing portions 46a are configured to form an O-ring. The thickness of these portions 46a may be in a range between 0.060 and 0.120 inches, with a thickness of 0.080 chosen for a preferred embodiment.

Figure 6:
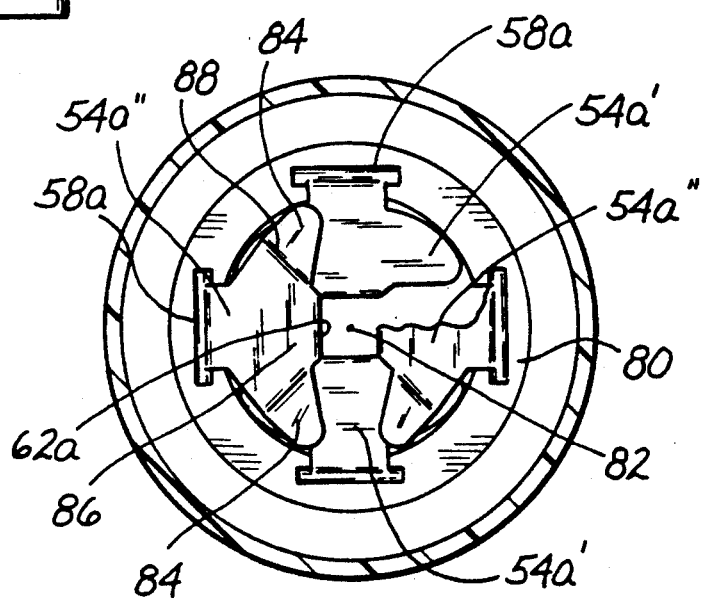
FIG. 6 is a top plan view of a further embodiment of the trocar valve assembly, showing a further hinge arrangement for the septum levers in a relatively closed configuration.
Figure 11:
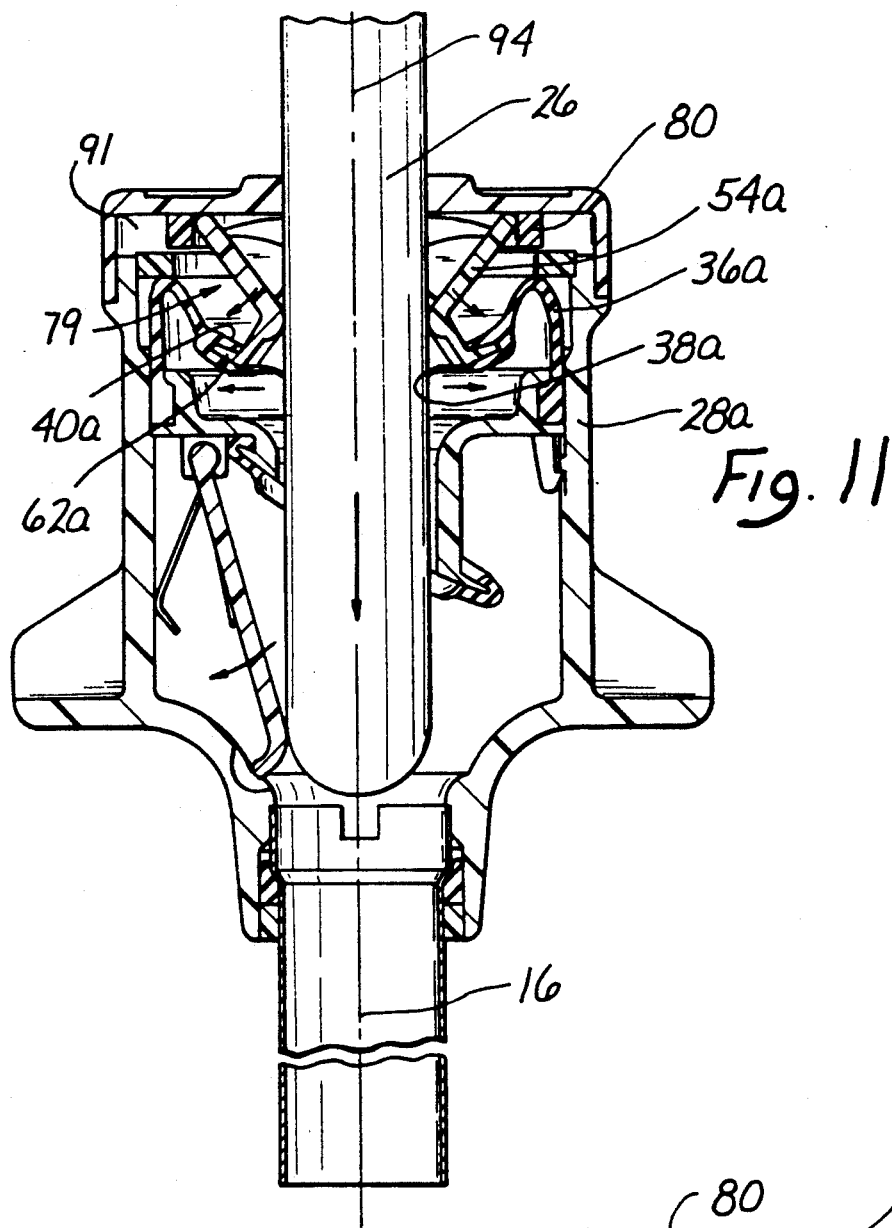
FIG. 11 is an axial cross-section view similar to FIG. 10 and illustrating the valve assemblies during insertion of the surgical instrument.

The actuation mechanism 79 illustrated in FIG. 6 including the frame 80 and levers 54a is particularly adapted for disposition in the trocar embodiment illustrated in FIG. 10. In this particular embodiment, the valve housing 28a defines an annular recess 91 which is configured to receive the ring 80 of the actuation assembly. The annular recess 91 is coaxial with the axis 16 of the trocar but is larger in diameter than the ring 80. As a result, the ring 80 is free to float within the recess 91.

This feature can best be understood by realizing that there are four axes associated with operation of this embodiment. These include an axis 94 associated with the instrument 26, the axis 16 associated with the housing 28a, the axis 82 associated with the actuation mechanism 79, and an axis 96 associated with the orifice 38. These four axes 16, 82, 94, and 96 are illustrated to be in alignment in FIG. 10. However, it is not uncommon for the instrument 26 to be inserted out of alignment with the housing 28a in which case the axis 94 is misaligned with the axis 16. In the past where the septum 36 was fixed within the housing 28 this misalignment of the instrument 28 tended to degrade the sealing characteristics of the septum 36. In order to enhance the integrity of the seal around the instrument 26, it is desirable that at least the axis 94 of the instrument 26 and the axis 96 associated with the orifice 38 be maintained in alignment. By providing the actuation mechanism 79 with floating characteristics, its axis 82 is automatically maintained in alignment with the axis 94 of the instrument 26. And since the lip 40a of the septum 36a is engaged by this actuation mechanism 79, the orifice 38 will also be maintained in alignment with the instrument 26. Thus the critical alignment between the instrument 26 and the orifice 38 can be maintained even if the instrument 26 is inserted out of alignment with the housing 28.

This floating characteristic of the actuation mechanism 79 is of particular advantage to the present invention. When the ring 80 is disposed centrally within the recess 91, the axis 82 associated with the mechanism 79 is concentric with the axis 16 of the trocar 10. However, if the ring 80 is permitted to float off-center within the recess 91, the axis 82 and and the axis 16 diverge. As result of this floating characteristic, the actuation mechanism 79, and the portions of the septum 36a which define the orifice 38, are free to move off-center from the housing. Furthermore this movement and resulting alignments occur before the instrument 26a even contacts the septum 36a. In the illustrated embodiment, if the instrument 26a is misaligned with the housing 28a, the actuation mechanism 79 and orifice 38a merely float into alignment with the instrument 26a. This alignment is automatically maintained, so the integrity of the seal is not jeopardized by the relative radial movement of the instrument 26 and the trocar 10.

Figure 8:
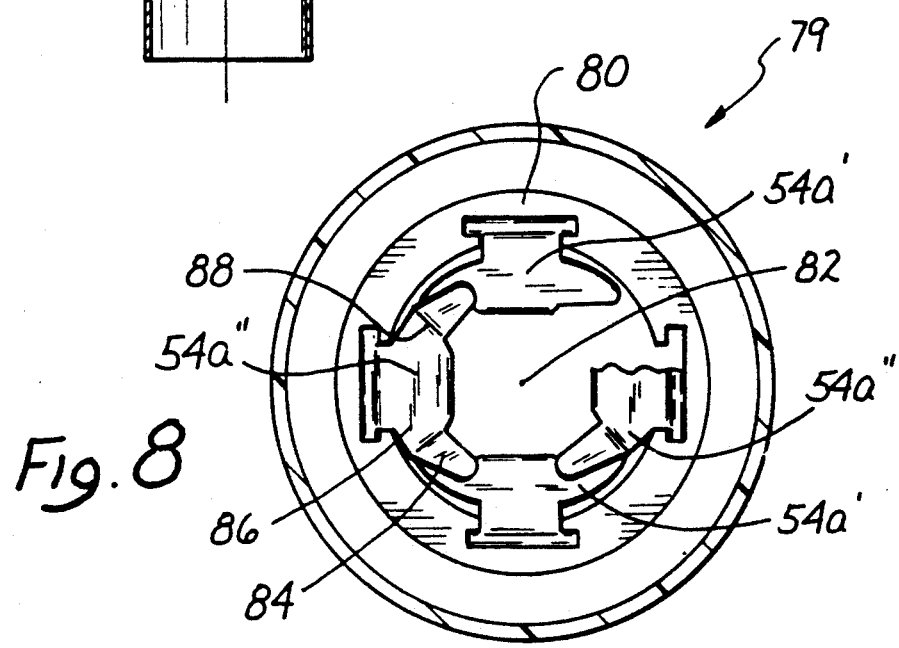
FIG. 8 is a top plan view similar to FIG. 6 and showing the septum levers in an expanded configuration.

Two positions of the levers 54a are shown in the figures. In FIG. 6 and 7, the levers are shown in their relaxed state, representing their position when no instrument is present in the channel. In FIGS. 8 and 9, the levers are shown in their pivoted state, wherein the lever teeth 62a have expanded the septum lip 40a upon entry of an instrument 26a into the channel. This embodiment may be preferred over the FIG. 2 embodiment because of its advantageous simplicity, reliability, and ease of manufacture.

As has been mentioned above, in addition to the two lever embodiments, two orifice embodiments are also contemplated. In a first embodiment, the first cross-sectional area of the orifice 38a in its relaxed state is substantially zero. This would ensure that leakage of gas from the abdominal cavity would be substantially eliminated when no instrument was inserted through the channel. In a second embodiment, the first cross-sectional area of the orifice 38a is greater than zero. This second configuration may be preferred under certain circumstances, such as when it is desired to utilize an instrument having a very narrow cross-section and a high degree of resiliency, e.g. a fiber optic tube. Such an instrument may be less capable of actuating the levers 54a to expand the orifice, being narrower than the channel throat 66a, but could still be used if the orifice in its relaxed state had a cross-section area greater than zero. The tradeoff is that removal of the instrument would permit a certain amount of continual leakage of gas from the abdominal cavity, although this leakage would be minimal since the orifice would be very small. Alternatively, a flapper valve 98 could be provided in the channel 24a in series with the septum 36a in order to stop this leakage in the absence of the instrument 26a.

The decision whether to employ the first or second orifice embodiment would rest upon considerations as to the type of instruments to be employed during the surgery, and the level of gas leakage which was deemed acceptable.

Although an exemplary embodiment of the invention has been shown and described, many changes, modifications, and substitutions may be made by one having ordinary skill in the art without departing from the spirit and scope of the invention.

We claim:

1. A trocar assembly having a channel defined along an elongate axis, the trocar assembly being adapted to receive an instrument having a particular cross-sectional dimension, said trocar assembly comprising:

an elastomeric septum disposed in said channel and including portions defining an orifice having in a relaxed state a first cross-sectional area and in an expanded state a second cross-sectional area; and means responsive to the particular dimension of the instrument for expanding said orifice to the second cross-sectional area.

2. The trocar assembly as recited in claim 1 wherein said first cross-sectional area is substantially zero.

3. The trocar assembly as recited in claim 1 wherein said first cross-sectional area is greater than zero.

4. The trocar assembly as recited in claim 1 wherein said second cross-sectional area is smaller than the particular cross-sectional area of said instrument.

5. The trocar assembly as recited in claim 1 wherein said elastomeric septum further comprises a lip positioned radially outwardly of the portions defining the orifice, said orifice expanding means engaging said lip and expanding it radially outwardly, thereby expanding said orifice.

6. The trocar assembly as recited in claim 1, and further comprising a seal housing adapted to receive the elastomeric septum, the septum having seating portions positioned radially outwardly of the orifice-defining portions and contiguous therewith, said seating portions being attached to said housing for seating the septum therein, wherein the seating portions are disposed in a first plane and said orifice-defining portions are disposed in a second plane, said first and second planes being spaced along said elongate axis.

7. The trocar assembly as recited in claim 6, wherein portions of said seal housing define an open space positioned radially outwardly of both the septum lip and the orifice expanding means such that when said orifice expanding means expands said lip, the lip expands into said open space.

8. A trocar assembly having a channel defined along an elongate axis, the trocar assembly being adapted to receive an instrument having a particular cross-sectional area, said trocar assembly comprising:

an elastomeric septum disposed in said channel and including portions defining an orifice having in a relaxed state a first cross-sectional area and in an expanded state a second cross-sectional area;

a lever having a distal end, and a proximal end pivotal on an axis transverse to the elongate axis of the trocar assembly;

means carried by the lever at said distal end for engaging the septum radially of the portions defining the orifice; and means disposed between the proximal end and the distal end of the lever for sensing the particular cross-sectional area of said instrument upon entry of said instrument into said channel, and moving the lever distal end a radial distance sufficient to expand the orifice to the second cross-sectional area.

9. The trocar assembly as recited in claim 8 wherein said elastomeric septum is comprised of a low durometer polymer.

10. The trocar assembly as recited in claim 9, wherein said low durometer polymer is C-flex ®.

11. The trocar assembly as recited in claim 8 wherein said elastomeric septum further comprises a lip positioned radially outwardly of the portions defining the orifice.

12. The trocar assembly as recited in claim 11 wherein said engaging means comprises a tooth at the distal end of said lever, said tooth being adapted to interlock with said septum lip, thereby engaging said septum.

13. The trocar assembly as recited in claim 12 wherein said orifice expanding means includes a plurality of said levers being substantially identical and being radially disposed about said elongate axis, with said channel being defined therebetween, and the tooth on each said lever being adapted to engage said lip on radially opposing ends of said septum.

14. The trocar assembly as recited in claim 13 wherein said septum lip comprises a substantially circular ridge circumscribing said septum, said lever teeth engaging said circular ridge.

15. The trocar assembly as recited in claim 14 wherein said lever teeth in aggregate comprise a substantially circular tooth member, said tooth member engaging said circular lip along its inner surface.

16. The trocar assembly as recited in claim 13 wherein each said lever has a predetermined radial width at the distal end and a predetermined radial width at the proximal end, said levers having an elbow-like configuration and being contoured radially inwardly from each end to a convergence point between said distal and proximal ends, such that the radial width of said channel narrows between said distal and proximal ends and is at a minimum width at said convergence point, said convergence point on said levers comprising said instrument diameter sensing means.

17. The trocar assembly as recited in claim 16 wherein said channel width at the convergence point is narrower than the particular cross-sectional area of said instrument, whereby when said instrument enters the channel and approaches the convergence point, it pushes said levers in a radially outward direction, thereby pivoting the levers about their proximal end pivot axes and pushing the distal ends of the levers radially outwardly, the engaging relationship between said distal end lever teeth and said septum lip thus pushing said lip radially outwardly and expanding said orifice.

18. A valve assembly adapted to receive an instrument having an outer surface and a cross-sectional dimension, comprising:

a housing defining a channel extending therethrough along an elongate axis;

a septum disposed in said housing and adapted to extend across said channel, portions of the septum defining an orifice communicating with the channel through the septum;

at least said portions of the septum being formed of an elastomeric material and being expandable radially outwardly to enlarge the orifice; and means pivotal on said housing and engaging the septum outwardly of the orifice for enlarging the orifice, said enlarging means being responsive to the instrument for enlarging the orifice in proportion to the cross-sectional dimension of said instrument.

19. The valve assembly recited in claim 18, wherein said orifice enlarging means includes:

a lever having a distal end, and a proximal end pivotal on an axis transverse to the elongate axis of said housing;

means carried by the lever at said distal end for engaging the septum radially of the portions defining the orifice; wherein said lever and said housing are integrally molded of a resilient elastomeric material, said lever pivoting on a living hinge at its proximal end.

20. The valve assembly as recited in claim 19, wherein said lever and said housing are integrally molded of nylon.

21. A seal assembly adapted to receive an elongate object and to form a seal around the object, the assembly comprising:
a housing defining a channel configured to receive the object moving generally axially through the channel;
a septum extending across the channel of the housing and forming an outer seal with the housing;
portions of the septum defining a hole communication with the channel on both sides of the septum, the hole having a size sufficient to receive the object with the hole portions forming an inner seal with the object;
the septum being formed of an elastomeric material having properties for producing a friction force which resists movement of the object through the septum; and
means responsive to insertion of the object into the channel for reducing the friction force on the object.

22. The assembly recited in claim 21 wherein the friction reducing means comprises:
means responsive to insertion of the object into the channel for measuring a particular dimension of the object; and
means for stretching the septum in proportion to the particular dimension to enlarge the hole and thereby reduce the friction forces between the septum portions and the object.

23. The assembly recited in claim 22 wherein:
the hole portions of the septum form an annular lip around the hole; and
the stretching means further comprises actuation means responsive to insertion of the object into the channel to move the annular lip a particular distance to enlarge the hole.

24. The assembly recited in claim 23 wherein the particular distance is a radial distance proportional to the particular dimension of the object.

25. The assembly recited in claim 22 wherein the friction reducing means further comprises:
a frame;
a plurality of levers each pivotal on the frame and engaging the septum to move the hole portions radially.

26. The assembly recited in claim 25 wherein the frame is annular and the friction reducing means is disposed transverse to the channel in the housing.

27. The assembly recited in claim 21 wherein:
the channel of the housing has a first axis;
the hole of the septum has a second axis; and
the septum is movable from a first position wherein the second axis is aligned with the first axis, to a second position wherein the second axis is not aligned with the first axis.

28. The assembly recited in claim 27 wherein:
the annular means of a third axis; and
the friction reducing means is movable from a third position wherein the third axis is aligned with the first axis, to a fourth position wherein the third axis is not aligned with the first axis.

29. A seal assembly adapted to receive an elongate object and to form a seal around the object, the assembly comprising:
a housing including first portions defining a channel extending through the housing, and second portions defining a peripheral recess in the housing;
a septum extending across the channel of the housing;
portions of the septum defining a hole adapted to receive the object with the septum portions forming a seal around the object;
the septum portions engaging the object through the channel;
actuation means movable within the peripheral recess of the housing for enlarging the hole in response to insertion of the object into the channel; whereby
the friction forces are reduced to facilitate further movement of the object through the channel of the housing.

30. The assembly recited in claim 29 wherein the actuation means includes a frame and means pivotal on the frame for moving the septum portions to enlarge the hole.

31. The assembly recited in claim 30 wherein:
the peripheral recess is an annular recess having a first diameter;
the frame of the actuation means has a second diameter; and
the first diameter is greater than the second diameter; whereby
that the actuation means is free to float in the peripheral recess.

32. The assembly recited in claim 30 wherein the moving means includes a plurality of levers each pivotal on the frame and positioned to engage the object and to move the hole portions of the septum a distance proportional to the size of the object.

* * * * *